United States Patent [19]
Nash

[11] Patent Number: 5,257,990
[45] Date of Patent: Nov. 2, 1993

[54] ELECTROSURGICAL CATHETER INSTRUMENT WITH IMPACTING WORKING HEAD AND METHOD OF USE

[75] Inventor: John Nash, Downingtown, Pa.

[73] Assignee: Kensey Nash Corporation, Exton, Pa.

[21] Appl. No.: 840,372

[22] Filed: Feb. 24, 1992

[51] Int. Cl.$^5$ ............................................. A61B 17/36
[52] U.S. Cl. ............................................. 606/45
[58] Field of Search ............................. 606/32, 36–40, 606/42–43, 45, 48–50

[56] References Cited

U.S. PATENT DOCUMENTS

| | | | |
|---|---|---|---|
| 4,637,390 | 1/1987 | Sorochenko | 606/50 |
| 4,660,571 | 4/1987 | Hess et al. | 606/49 |
| 5,015,227 | 5/1991 | Broadwin et al. | 606/45 |

Primary Examiner—Lee S. Cohen
Assistant Examiner—Marianne Parker
Attorney, Agent, or Firm—Caesar, Rivise, Bernstein, Cohen & Pokotilow, Ltd.

[57] ABSTRACT

Apparatus and a method for cauterizing and/or removing or debulking tissue located on the surface or within the body of a living being. The apparatus comprises a catheter having a distal end portion at which a working head is located. The working head is arranged to be moved, e.g., rotated, repeated by a drive system including an electrically conductive cable. The cable is connected between the working head and one electrode of an electrosurgical power supply. The other electrode of the supply is connected to a plate arranged to engage a portion of the being's skin. The working head is arranged to be located adjacent the biological material and to be rotated at a relatively high speed to sweep a localized intense electrical current (e.g., arc) across a portion of tissue located immediately adjacent the working head. The repeated movement of the working head impacts the tissue to debulk it.

21 Claims, 3 Drawing Sheets

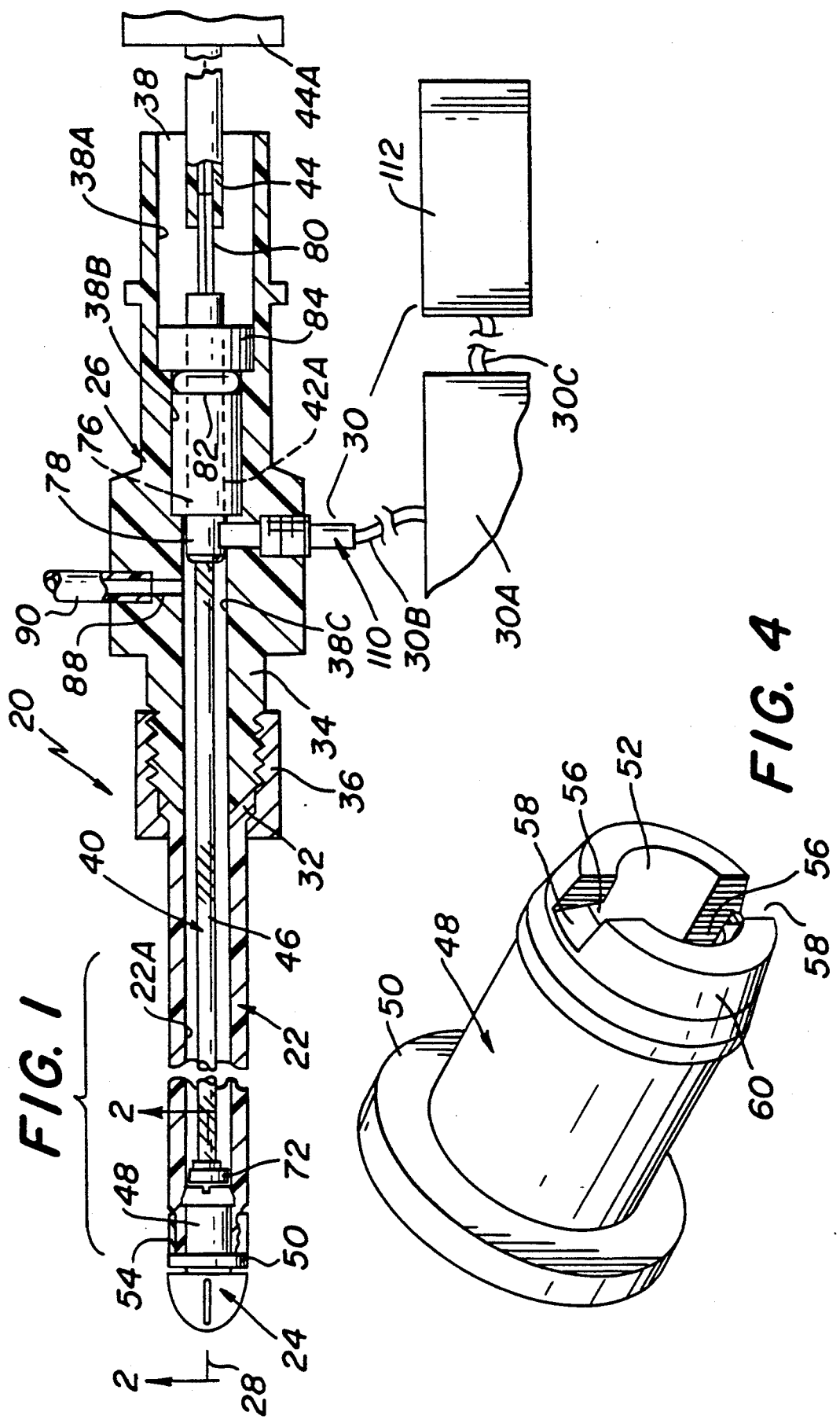

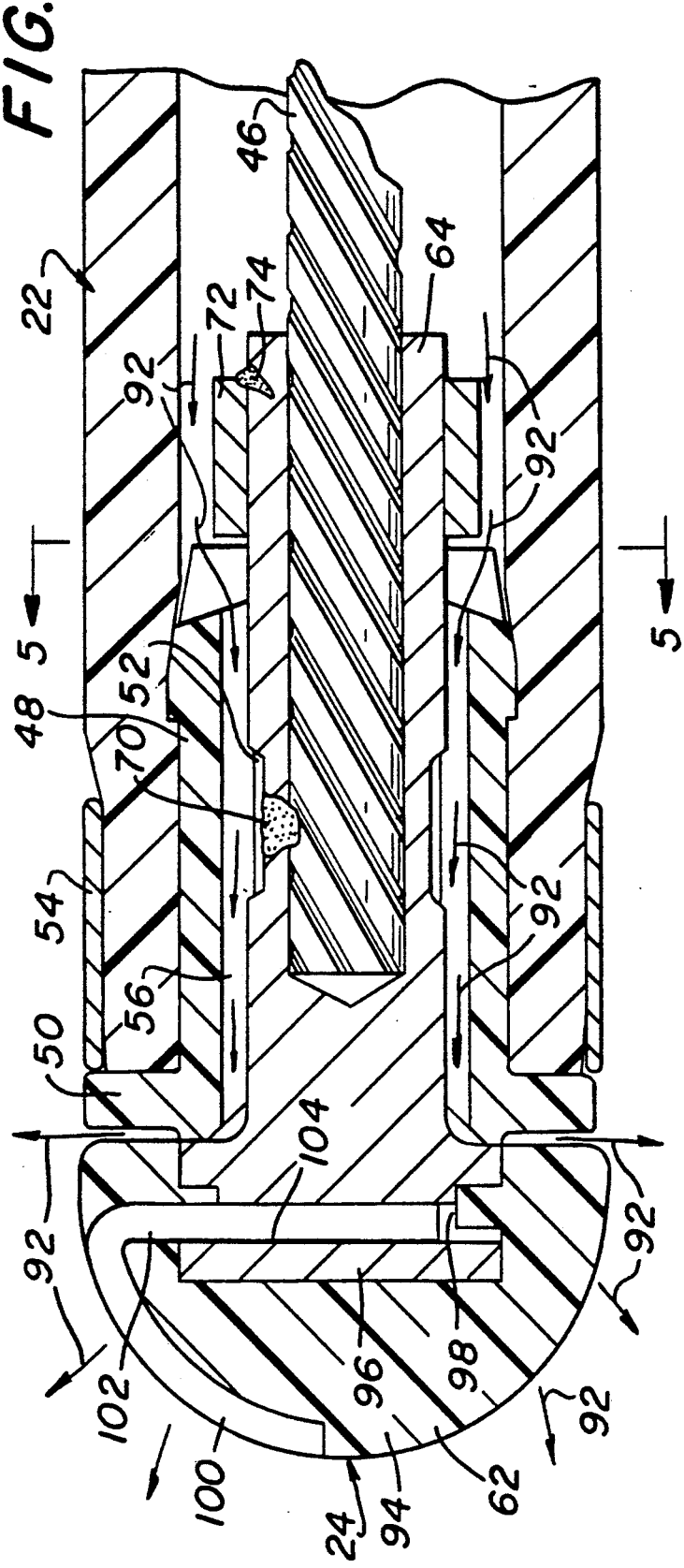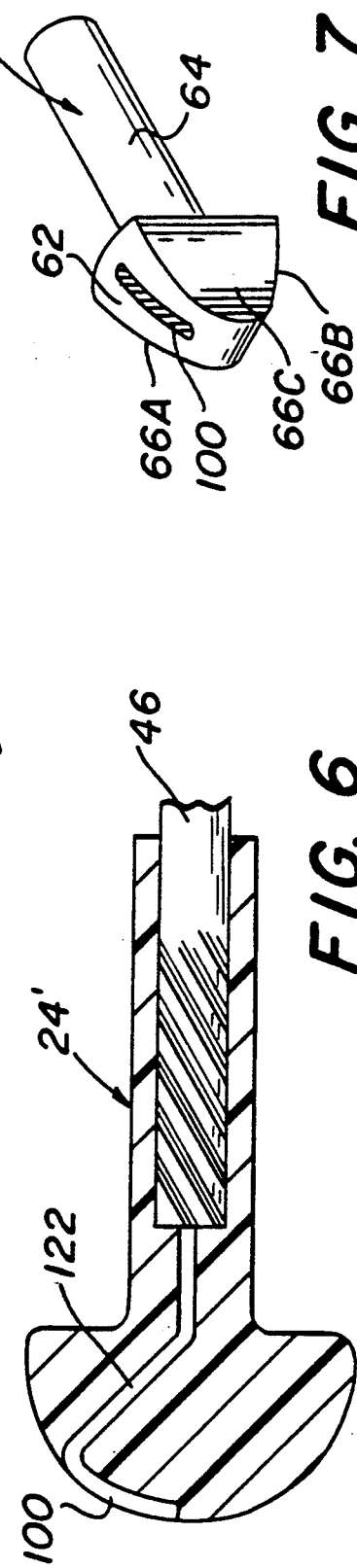

ELECTROSURGICAL CATHETER INSTRUMENT WITH IMPACTING WORKING HEAD AND METHOD OF USE

This invention relates generally to medical devices and procedures, more particularly to apparatus and methods for applying an electrical energy to biological material on or within the body of a living being to effect the burning or cauterization of such material alone or in combination with the debulking or removal thereof.

BACKGROUND OF THE INVENTION

The prior art includes various diathermic devices for burning, cutting, and cauterizing tissue within the body of a patient. One such device is commonly referred to as an electrosurgical instrument. That instrument typically includes one electrode, in the form of a small operating tip which is connected to one, e.g., the positive, terminal of an electrosurge generator, e.g., a high frequency electrical source. The tip is arranged to be brought into engagement or very close proximity to the tissue to be treated so that an intense (dense) electric current or arc is produced between the instrument's tip and the tissue. In order to complete the electrical circuit, the other, e.g., negative, terminal of the generator is normally connected to a rather large plate electrode (typically grounded) in electrical contact with the skin of the patient. As discussed in U.S. Pat. No. 4,034,761 (Prater et al.), the electrical signals provided by the generator may be of different characters to effect a different procedure. Thus, the signals may be of the type referred to as "cutting signals" for effecting the cutting of tissue by destroying (e.g., burning) the tissue cells adjacent the electrode tip. The signals may also be of the type referred to as "coagulation or hemostasis signals" for dehydrating or shrinking of blood vessel walls around a contained clot of coagulated blood, thereby fusing the vessel to seal off the flow of blood. The generator may produce a blend of the cutting and coagulating signals, such combined signals (sometimes referred to as "fulguration or blended signals") is used to effect cutting and coagulation at the same time.

Other examples of electrical devices for effecting both cutting and coagulation or either operation are found in the following U.S. Pat. Nos.: Re. 29,088 (Shaw); Re. 30,190 (Shaw); 2,447,169 (De Sousa); 3,336,916 (Edlich); 3,648,001 (Anderson et al); 3,911,241 (Jarrard); 4,089,336 (Cage et al); 4,091,813 (Shaw et al); 4,112,950 (pike); 4,185,632 (Shaw); 4,311,145 (Esty et al); 4,362,160 (Hiltebrandt); 4,638,802 (Okada); 4,375,218 (DiGeronimo); 4,427,006 (Nottke); 4,481,057 (Beard); 4,562,838 (Walker); 4,640,279 (Beard); 4,646,738 (Trott); 4,674,498 (Stasz); 4,793,346 (Mindich); 4,802,476 (Noerenberg et al); 4,903,696 (Stasz et al); 4,922,903 (Welch et al); 4,850,353 (Stasz et al); and 5,013,312 (Parins et al).

While such prior art devices are generally suitable for their intended purposes, they never the less leave much to be desired from the standpoint of usefulness for a wide range of applications. For example, such prior art devices are not well suited for effectively debulking and cauterizing tissue within the body of the being via a small natural orifice or small percutaneous incision or puncture during laparoscopic or endoscopic procedures.

OBJECTS OF THE INVENTION

Accordingly, it is the general object of this invention to provide an apparatus and a method of use which overcomes the disadvantages of the prior art.

It is a further object of this invention to provide apparatus and a method of use for effecting cauterization and/or other procedures on biological material on or within the body of a living being.

It is another object of this invention to provide apparatus and a method of use for effecting cauterization and/or other procedures on biological material via a small natural opening or a small percutaneous incision or puncture.

It is still a further object of this invention to provide an electrosurgical apparatus which is of wide utility.

SUMMARY OF THE INVENTION

These and other objects of the instant invention are achieved by providing apparatus and methods for effecting some medical procedure on biological material or tissue located on the exterior surface or within the body of a living being.

The apparatus comprises an instrument, e.g., a catheter, having a distal end portion at which a working head is located, drive means, and power means. The working head is arranged to be located e.g., introduced percutaneously or through a natural orifice, immediately adjacent the biological material (e.g., tissue) to be treated and once so located is repeatedly moved, e.g., rotated, at a relatively high speed with respect thereto. The power means is arranged to provide electrosurgical current to the working head, whereupon an intense localized flow of electrical current (e.g., an arc) is swept across a portion of the biological material.

In accordance with one preferred embodiment of this invention the working head includes surface portions arranged to repeatedly impact the biological material, e.g., highly vascular tissue, to debulk it while the arc cauterizes it.

DESCRIPTION OF THE DRAWING

Other objects and many of the attendant advantages of this invention will be readily appreciated as the same becomes better understood by reference to the following detailed description when considered in connection with the accompanying drawing wherein:

FIG. 1 is a side elevational view, partially in section, of an electrosurgical apparatus constructed in accordance with this invention;

FIG. 2 is an enlarged sectional view taken along lines 2—2 of FIG. 1 and showing one embodiment of a working head of the subject apparatus;

FIG. 4 is an enlarged isometric view of one of the components making up the apparatus shown in FIG. 1;

FIG. 6 is a reduced, sectional view of an alternative working head of the subject apparatus; and FIG. 7 is a reduced, isometric view of a working head of the subject apparatus.

DETAILED DESCRIPTION OF THE PREFERRED EMBODIMENT

Figure 3:
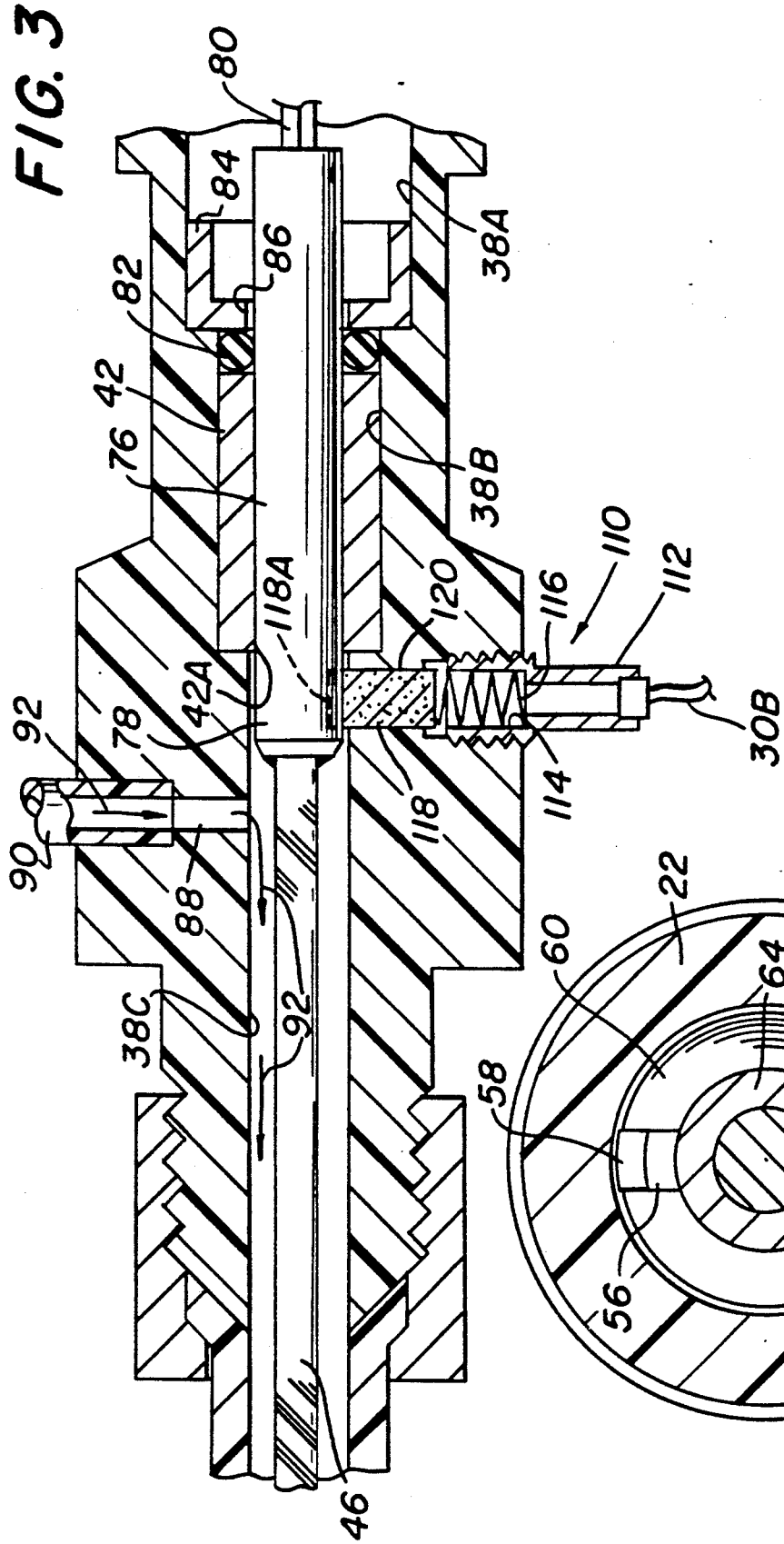
FIG. 3 is an enlarged sectional view of a portion of the apparatus shown in FIG. 1.
Figure 5:
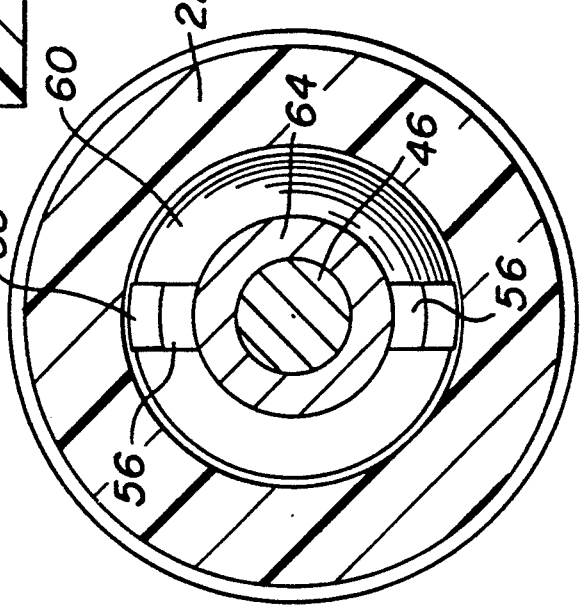
FIG. 5 is a sectional view taken along lines 5—5 of FIG. 2.

Referring now in detail to the drawing wherein like reference characters refer to like parts, there is shown at 20 in FIG. 1 apparatus constructed in accordance with the subject invention.

The apparatus 20 is preferably in the form of a catheter instrument for introduction via a man-made opening, e.g., a percutaneous incision or puncture, or via a natural opening or orifice, e.g., the urethra, into the body of a patient to effect some medical procedure, e.g., debulking of the patient's prostate, kidney, liver, etc. The instrument can also be used to effect some medical procedure on the outer surface, e.g., skin, of the being. In any case the instrument 20 basically comprises an elongated tubular jacket portion 22, a working head 24, and a body portion 26. The working head 24 is located at the distal end of the tubular jacket 22 and is arranged to be repeatedly moved, e.g., rotated, oscillated, etc., at a relatively high rate of speed with respect to the central longitudinal axis 28 of the catheter by a motor (not shown) forming a part of a drive assembly 40 (to be described later) located within the catheter's body 26. In the preferred embodiments shown herein the working head is rotated about the central axis. That is merely one exemplary type of movement. Thus, the working head may be repeatedly moved or scanned through any shape of path by any suitable drive mechanism.

In any case the working head is arranged to be brought into engagement or very close proximity to the biological material to be treated and then repeatedly moved or scanned thereacross. In the exemplary embodiments of the working heads shown and described herein, each includes a pair of impacting surfaces (to be described later), which when the working head is rotated, repeatedly impact the biological material (e.g., tissue) to be treated, to emulsify it into small pieces or particles, thereby debulking it.

The instrument 20 includes electrosurgical means 30 for effecting cauterization or hemostasis of internally located tissue. This feature is of considerable importance, particularly in applications wherein the material being impacted or debulked is highly vascular tissue, e.g., the prostate, liver and kidney.

As can be seen clearly in FIG. 1, the jacket portion 22 of the catheter comprises a thin walled tube formed of any suitable material having good electrical insulating properties, e.g., plastic, and has a small outside diameter In the preferred embodiment herein, the outside diameter is approximately 2.25 mm (8 French). This size is merely exemplary. Thus, the jacket 22 may be either smaller or larger, depending upon the application to which the catheter 20 will be put.

The proximal end of the jacket 22 is in the form of a flared flange 32 which is arranged to be connected to the proximal end 34 of the catheter's body portion 26 via a threaded cap 36. The body portion 26 is a generally hollow, electrically insulating, member including a central passageway 38 extending therethrough. It is within this passageway that the drive assembly 40 for the catheter is located. The passageway 38 includes three sections, 38A, 38B and 38C, each of different internal diameter. The distal-most section 38C has an internal diameter which is the same as the hollow passageway 22A extending through the catheter jacket 22. In fact, passageway section 38C is essentially coaxial with the hollow interior 22A of the jacket 22. The middle section 38B of the passageway 38 is of larger internal diameter than section 38C and is arranged for receipt of a bushing 42 (to be described later) therein. The bushing 42 also forms a portion of the drive assembly 40. The proximal end of the passageway 38 includes an even larger internal diameter section 38A. This section is arranged for receipt of the output drive shaft 44 of the instrument's motor 44A (FIG. 1).

The catheter's body 26 and the threaded sleeve 36 are each formed of a tough, strong, electrically insulating material, e.g., polycarbonate. The jacket portion 22 is also formed of electrically insulating material. The jacket may be flexible, depending upon the application to which the instrument will be put, e.g., flexible for arterial stenotic debulking, rigid for prostate debulking. Thus, in accordance with one preferred aspect of this invention the jacket is formed of Teflon or polyethylene tubing.

A bushing 48 is mounted at the distal end of the catheter's jacket 22 (see FIGS. 2 and 4). The body of the bushing has a peripheral flange 50 and a central bore 52 passing longitudinally therethrough. The proximal end of the bushing is in the form of a thrust pad 60.

The body of the bushing is mounted within the distal end of the passageway 22A in the jacket so that its flange 50 abuts the free end of the jacket 22. The outside diameter of the bushing's body is approximately the same as the inside diameter of the passageway in the jacket so that it is snugly fix therein. A retaining band 54 tightly encircles the outer periphery of the catheter's jacket to hold the bushing tightly in place. When so mounted, the central bore 52 of the bushing is axially aligned with the central longitudinal axis 28 of the catheter.

The bushing 48 also includes a pair of radially located grooves 56. Each groove extends longitudinally down the length of the bore 52. The grooves are diametrically opposed from each other. The grooves and the interposed bore form a slot through which a liquid (e.g., deionized or distilled non-conducting water) which is used to lubricate the drive assembly 40 flows (as will be described later). In order to enable that liquid to flow through the bushing each groove includes an axial groove or inlet slot 58 at its proximal end. The distal end of each groove 56 is open at the free end of the catheter.

In accordance with the preferred embodiment of this invention, the bushing 48 is formed of an electrically insulating material, e.g., Torlon (a polyetherimide).

Any type of working head can be utilized in the catheter 20. In the embodiment shown herein, the working head 24 is constructed generally in accordance with the teachings of U.S. Pat. No. 4,747,821, entitled "Catheter With High Speed Moving Working Head", which is assigned to the same assignee as this invention and whose disclosure is incorporated by reference herein. However, the working head 24 of this invention includes electrically insulating and electrically conductive portions, not disclosed in that patent in order to form a portion of the electrosurge means 30.

The details of one embodiment of the working head 24 will now be described with reference to FIGS. 1, 2 and 7. As can be seen therein, that working head basically comprises a convex crown 62 and a mounting shank 64. The working head is mounted in the catheter's distal end so that its shank, which projects proximally from it crown, passes into the bore 52 in the bushing 48 at the distal end of the catheter. The crown 62 includes a pair of non-sharp impacting surfaces 66A and 66B. These surfaces are arranged to repeatedly impact the biological material, e.g., tissue, to be treated when the working head is rotated (or oscillated) about longitudinal axis 28 to pulverize or emulsify that material into very small-sized particles as described in the heretofore identified U.S. Pat. No. 4,747,821. The impacting surfaces 66A and 66B are formed by rounded or radius edges at the interface of the outer convex surface of the working head's crown and a respective pair of relieved, e.g., flatted, surfaces 66C. The width of the working head 24 between the flatted surfaces 66C is approximately that of the diameter of the shank portion 64 and is less than the width of the slot formed by the grooves 56 and the interposed passageway 52 in the bushing 48. Accordingly, the distal end of each groove 56 will be periodically exposed by the rotation (or oscillation) of the working head. This action enables the liquid, e.g., distilled water, which is used to lubricate the drive assembly, to exit from the distal end of the catheter through the interface between the distal end of the bushing and the working head (as will be described later).

The drive assembly is arranged to rotate the working head at various rates of speed, e.g., from 10,000 rpm to 250,000 rpm. To that end, the shank 64 of the working head 24 is connected to the distal end of the drive cable 46. In particular, the shank 64 includes the central bore into which the distal end of the cable 46 extends. The cable may comprise a single filament or multi-filaments and is welded in place within the central bore by a weldment 70. The longitudinal position of the working head with respect to the catheter is fixed by means of a sleeve 72 which is welded by a weldment 74 to the proximal end of the working head shank 64. This sleeve is arranged to bear against the thrust pad 60 of the bushing through a layer of lubricating liquid (i.e., water) introduced into the system, as will be described later.

The details of the drive assembly 40 will now be considered with reference to FIGS. 1-3. Thus, it can be seen therein the drive assembly 40 basically comprises the heretofore identified drive cable 46, the heretofore identified drive motor (not shown), the heretofore identified rotary output shaft 44, and a coupling 76. The coupling 76 serves to connect the drive cable to the rotary output shaft 44 of the motor.

As best seen in FIG. 3, the coupling 76 basically comprises an elongated rod-like member having a distal end portion 78 of circular outer periphery and a proximal end portion 80 of square outer periphery. The proximal portion 80 of the coupling is arranged to be disposed within a correspondingly shaped bore 44A in the output drive shaft 44 of the motor.

The motor may be any conventional device which, when operated, causes its output drive shaft to rotate about the longitudinal axis 28 of the catheter. Thus, when the motor is operated and its drive shaft 44 rotating, such rotation is transmitted by the coupling 76 and the drive cable 46 to the working head 24.

In order to support the coupling at a centered position within the catheter, i.e., axially aligned with central longitudinal axis 28, the circular peripheral portion 78 of the coupling 76 is located within a central bore 42A of the heretofore identified bushing 42.

An O-ring 82 extends about the periphery of the coupling portion 78 immediately adjacent the distal end of the bushing 42. The O-ring 82 is retained in position within the passageway section 38B by means of a cup-shaped retaining cap 84. The cap 84 is snugly fit within the passageway section 38A. The retaining cap 84 includes a central opening 85 through which the coupling 76 extends. The O-ring 82 serves as a seal to prevent the egress of the water introduced into the interior passageway 38C of the catheter from flowing proximally into passageway section 38A and towards the motor.

The water for lubricating the drive system is introduced via a port 88 in the housing section 26 contiguous with passageway section 38C. A flexible conduit or pipe 90 is connected to the port 88 to carry the water from an electrically insulated source (not shown). The water enters into the catheter 20 via the conduit 90 and associated port 88 and flows through the catheter in the direction of arrows 92 in FIGS. 2 and 3. Thus, as can be seen therein, the water flows down the passageway section 38C through the hollow interior of the catheter jacket 22 into the radial slots or inlets 58 and the communicating grooves 56 down the length of the bushing 48. The water exits from each groove at its open distal end whenever the working head has rotated to a position where it's crown no longer covers the end of that groove. Thus, the water exiting from the catheter 20 is in the form of plural jets, each of which is immediately accelerated laterally by the flatted surfaces 66C of the working head, so that the jets are broken up into small segments or slugs that develop considerable momentum as they are flung radially outward (See the arrows 92 in FIG. 2). This action helps establish a toroidal flow of liquid adjacent the working head to carry particles of the biological material broken away by the impacting action back into engagement with the impacting surfaces to further reduce the size thereof.

The electrosurge means 30 mentioned heretofore is coupled to the working head so that as the working head is rotated or oscillated a high density current, e.g., arc, which is localized at the working head, is swept across the biological material or tissue contiguous with the working head as the working head moves. Thus, the working head 24 forms a portion of the electrosurge system 30. The cable 46 and the coupling 76 also form a portion of that system. To that end, the cable and coupling are each formed of an electrically conductive material, e.g., stainless steel, to form an electrical circuit path to the working head 24. Electrical energy from a conventional electrosurge generator (to be described later) is provided to the coupling 76 by means (also to be described later).

The working head can be formed in various ways to provide an electrically conductive surface which is in electrical continuity with the drive cable. One such arrangement is shown in FIG. 2. As can be seen therein, the crown of the working head 24 is in the form of a cap 94 of an electrically insulating material, e.g., plastic, which is secured onto the shank portion 64 of the working head. The shank portion 64 is formed of an electrically conductive material, e.g., stainless steel. In order to secure the cap to the shank, the shank includes a retaining flange 96 at its distal end. The flange has a peripheral groove 98 arranged to receive a correspondingly shaped annular projection in the cap 96.

An electrically conductive material, e.g., stainless steel, strip 100 is mounted within the cap 94 so that a portion of the outer surface of the strip is flush with the convex outer surface of the cap. That portion of the strip is oriented so that it extends almost 90° from a location immediately adjacent the central axis 28 at the top of the crown backward to a point close to the rear face of the crown. The strip 100 also includes a portion 102 extending radially inward from the outer surface of the cap into a diametric slot 104 located in the retaining flange 96 of the shank of the working head so that the strip is electrically connected to the working head shank, and from there to the drive cable 46.

The generator for supplying the electrosurgical energy is denoted by reference numeral 30A in FIG. 1 and can be of any suitable construction to provide any type of electrical signal, as desired. In the exemplary embodiment shown herein, the generator 30A includes a positive or "hot" terminal connected, via a cable 30B, to a brush assembly 110. The brush assembly will be described later. Suffice it for now to state that the brush assembly is arranged to carry the electrical energy from cable 30B to the coupling 76 and from there via the drive cable 46 to the working head, and in particular its conductive strip 100. The other terminal of the electrosurge generator 30A is connected, via a cable 30C, to a conventional plate electrode 112. The plate electrode 112 is an electrically conductive member having a large surface area which is arranged to be held in contact with the skin of the patient to complete the electrosurgical circuit.

Referring now to FIG. 3, the details of the brush assembly 110 will be described. As can be seen, the brush assembly 110 basically comprises an electrically conductive externally threaded plug 112. The plug extends into a correspondingly threaded bore 114 in the sidewall of the body 26. The cable 30B is electrically connected to the plug 112. The plug 112 includes a hollow bore 114 in which is disposed an electrically conductive helical compression spring 116. The spring 116 is seated on a seat formed by the base of the hollow bore 114 in the plug 112. An electrically conductive brush 118 is located within a radially extending bore section 120 in the catheter body 26. The brush 118 is formed of any suitable electrically conductive material, e.g., beryllium copper, and has an arcuate recess 118A at its inner end. The brush 118 is arranged to be engaged by the spring 116 to bias it radially inward toward the coupling 76 so that its arcuate end 118A, rides on the outer surface of the cylindrical portion 78 of the coupling 76. Accordingly, the electrical energy provided via cable 30B from generator 30A is coupled via the brush 118 to the coupling 76 and from there through the drive cable 46 to the conductive strip 100 of the working head 24. The motor is electrically insulated from the output drive shaft 44.

Depending upon the procedure to be effected, the electrosurge generator 30A can be operated at the same time that the working head is repeatedly moved, e.g., rotated, with the impacting surfaces engaging the biological material to be debulked so that as the material is debulked hemostasis is effected. Alternatively, the catheter 20 may be used with the working head debulking the biological material, but with the electrosurge system off. When it is desired to effect the hemostasis or cauterization the electrosurge system can be turned on.

In FIG. 6 there is shown an alternative embodiment 24' of the working head. The working head 24' is similar in most respects to the working head 24 of FIG. 7 except that its crown and shank portions are form as an integral unit of an electrically insulating material, e.g., plastic. Moreover, the electrically conductive strip 100 includes an internal section 122 which extends radially inward into the crown and then along the central longitudinal axis 28 of the shank to the bottom of the bore in which the distal end of the drive cable 46 is located. At that point the section 122 of the electrically conductive strip 100 is electrically connected, e.g., welded, to the drive cable 46.

It should be pointed out at this juncture that the two working heads described heretofore are merely exemplary. Thus, other constructions for the working head are contemplated within the scope of this invention.

It should also be understood that the device described utilizes what is known as a monopolar electrosurge system where the return current flows via a plate in contact with the patient, usually at the skin. Other constructions are also contemplated using a bipolar system, where the return current passes along a conductor close to the supply conductor, having entered at a return electrode placed quite close to the supply electrode and touching tissue close to the supply electrode.

Without further elaboration, the foregoing will so fully illustrate my invention that others may, by applying current or future knowledge, readily adopt the same for use under various conditions of service.

What is claimed is:

1. An apparatus for debulking soft biological material located within a body, said apparatus comprising:
    an elongated member having a longitudinal axis and comprising a distal end portion configured to be passed through a small opening in the body of said being, said opening being either formed by a percutaneous incision or puncture or being a natural body opening, whereupon said distal end portion is located completely within the body of said being
    a working head disposed at said distal end portion for location adjacent said biological material, said working head including impaction means for repeatedly impacting said biological material;
    drive means including motor means coupled to said working head, said motor means for operating said drive means; said drive means for repeatedly moving said working head in a predetermined arcuate path about said longitudinal axis, whereupon said movement of said working head in said predetermined arcuate path causes said impaction means to repeatedly impact said material to debulk it; and
    electrosurgical generator means providing electrosurgical energy to said working head, whereupon the movement of said working head in said path about said axis sweeps a localized intense electric current across a portion of said material which is located immediately adjacent said working head.

2. The apparatus of claim 1 wherein said working head includes at least one portion formed of an electrically conductive material.

3. The apparatus of claim 1 wherein said movement of said working head constitutes rotation about said axis.

4. The apparatus of claim 1 wherein said movement of said working head through said arcuate path is accomplished by rotating said working head about said axis, whereupon said rotation of said working head about said axis causes said impaction means to repeatedly impact said material.

5. The apparatus of claim 1 wherein said elongated member comprises a tubular portion formed of an electrically insulating material, and a body portion formed of an electrically insulating material.

6. An apparatus for effecting some procedure on some biological material located on an outer surface of a body or within the body, said apparatus comprising:
    an elongated member of a small diameter for insertion into a percutaneous incision, having a longitudinal axis and comprising a distal end portion;

a working head disposed at said distal end portion for location adjacent said biological material;

drive means comprising motor means and an elongated rotatable drive member, said motor means for operating to said drive member, said drive member being connected to said working head, said drive member comprising an electrically conductive material and operating under control of said motor means for repeatedly rotating said working head through an arc about said longitudinal axis; and electrosurgical generator means electrically connected to said drive member for providing electrosurgical energy to said working head, whereupon the rotation of said working head sweeps a localized intense electric current across a portion of said material which is located immediately adjacent said working head.

7. The apparatus of claim 6 wherein said working head includes at least one electrically conductive portion in electrical continuity with said drive member, and wherein said apparatus additionally comprises brush means, coupled to said electrosurgical generator means and engaging a potion of said drive member as said drive member is rotated, for electrically connecting said electrosurgical generator means to said drive member.

8. The apparatus of claim 7 wherein said electrosurgical generator means comprises two electrodes, one of said electrodes being electrically connected to said brush means, the other of said electrodes being electrically connected to an electrically conductive member arranged to be placed in contact with said biological material.

9. An apparatus for debulking some biological material located on an outer surface of a body or within the body, said apparatus comprising:

an elongated member of a small diameter for insertion into a percutaneous incision, having a longitudinal axis and comprising a distal end portion;

a working head disposed at said distal end portion for location adjacent said biological material, said working had including impaction means for repeatedly imparting said biological material;

drive means including motor means for operating said drive means and an elongated rotatable drive member, said drive member comprising an electrically conductive material and being connected to said working head; said drive means for rotating said working head about said longitudinal axis whereupon said rotation of said working had about said axis causes said impaction means to repeatedly impact said material; and electrosurgical generator means electrically connected to said drive member for providing electrosurgical energy to said working head, whereupon the rotation of said working head about said axis weeps a localized intense electric current across a portion of said material which is located immediately adjacent said working head.

10. The apparatus of claim 9 wherein said working head includes at least one electrically conductive portion in electrical continuity with said drive member, and wherein said apparatus additionally comprises brush means, coupled to said electrosurgical generator means and engaging a potion of said drive member as said drive member is rotated, for electrically connecting said electrosurgical generator means to said drive member.

11. The apparatus of claim 10 wherein said electrosurgical generator means comprises two electrodes, one of said electrodes being electrically connected to said brush means, the other of said electrodes being electrically connected to an electrically conductive member arranged to be placed in contact with said being.

12. An apparatus for effecting some procedure on some biological material located on an outer surface of a body or within the body, said apparatus comprising:

an elongated member of a small diameter for inserting into a percutaneous incision having a longitudinal axis and comprising a distal end portion;

a working head disposed at said distal end portion for location adjacent said biological material;

drive means, including means for operating said drive means and an elongated drive member, said drive member being coupled to said working head for repeatedly moving said working head in a predetermined path with respect to said longitudinal axis under control of said motor means, wherein said movement of said working head with respect to said axis constitutes rotation through multiple complete revolutions about said axis, all of said revolutions being in a single rotational direction; and electrosurgical generator mans providing electrosurgical energy to said working head, whereupon the rotation of said working head sweeps a localized intense electric current across a portion of said material which is located immediately adjacent said working head.

13. A method of performing a medical procedure on biological material located within a body comprising;

providing an elongated instrument of small diameter and having a longitudinal axis terminating in a distal end portion at which a working head is located;

introducing a portion of said instrument through a small opening in the body so that said working head is located adjacent said biological material;

repeatedly moving said working head through a predetermined path with respect to said axis and with respect to said biological material; and providing electrosurgical energy to said working head and through a portion of the body to sweep a localized intense electrical current across a portion of said biological material which is located immediately adjacent said working head.

14. The method of claim 13 additionally comprising the step of causing at least one portion of said working had to repeatedly impact said biological material as said working head is moved through said path.

15. The method of claim 14 wherein said repeated impacting of said material debulks it.

16. The method of claim 14 wherein said electrosurgical energy is provided to said working head as said working had repeatedly impacts said material.

17. The method of claim 13 wherein said opening is formed by a percutaneous incision or puncture.

18. The method of claim 13 wherein said opening is a natural body opening or orifice.

19. The method of claim 13 wherein said material is selected from the group comprising the prostate, liver, and kidney.

20. The method of claim 13 wherein the movement of said working head through said path constitutes rotation about said axis.

21. The method of claim 20 wherein said rotation constitutes multiple complete revolutions about said axis, with all of said revolutions being in a single rotational direction.

* * * * *